United States Patent [19]

Müller et al.

[11] Patent Number: 5,071,933
[45] Date of Patent: Dec. 10, 1991

[54] ADHESIVE COMPONENTS CONTAINING ALKANEDIYL-BIS-CARBOXAMIDES FOR THE TREATMENT OF COLLAGEN

[75] Inventors: Michael Müller, Bergisch Gladbach; Wolfgang Podszun, Cologne, both of Fed. Rep. of Germany

[73] Assignee: Bayer Aktiengesellschaft, Leverkusen, Fed. Rep. of Germany

[21] Appl. No.: 575,037

[22] Filed: Aug. 30, 1990

[30] Foreign Application Priority Data

Sep. 21, 1989 [DE] Fed. Rep. of Germany ....... 3931418

[51] Int. Cl.$^5$ .................. C08F 120/58; C08F 122/38; A61K 6/08; A61C 5/00; A61C 69/52
[52] U.S. Cl. .................................... 526/304; 526/310; 523/116; 433/228.1; 560/222
[58] Field of Search ............. 526/304; 433/215, 228.1; 523/116; 560/222

[56] References Cited

U.S. PATENT DOCUMENTS 4,192,784 3/1980 Brown et al. ...................... 526/304
4,732,943 3/1988 Beech et al. ...................... 525/303

*Primary Examiner*—Joseph L. Schofer
*Assistant Examiner*—Wu C. Cheng
*Attorney, Agent, or Firm*—Sprung Horn Kramer & Woods

[57] ABSTRACT

In the application of an adhesive component to a collagen-containing material such as tooth or a bone, the improvement wherein the adhesive component comprises a compound of the formula

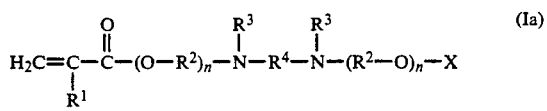 (Ia)

in which
$R^1$ denotes hydrogen or methyl,
$R^2$ and $R^4$ denote divalent aliphatic radicals having one to three carbon atoms,
$R^3$ denotes hydrogen or formyl (—CO—H),
X denotes hydrogen or (meth)acryloyl

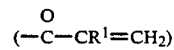

and
n represents 0 or 1, with the proviso that if $R^3$ equals H, n is zero.

Those compounds are new in which $R^3$ denotes formyl and n represents 1.

10 Claims, No Drawings

ADHESIVE COMPONENTS CONTAINING ALKANEDIYL-BIS-CARBOXAMIDES FOR THE TREATMENT OF COLLAGEN

The invention relates to new alkanediyl-bis-carboxamides (I) and preparations (II) which contain compounds (Ia) for use as an adhesive component for the treatment of collagen-containing materials, and to processes for the production and the use of the preparations (II).

The new alkanediyl-bis-carboxamides correspond to the formula (I)

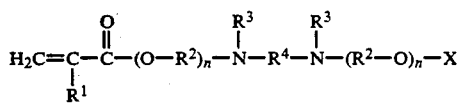

in which
R$^1$ denotes hydrogen or methyl,
R$^2$ and R$^4$ denote divalent aliphatic radicals having two or three carbon atoms,
R$^3$ denotes formyl (—CO—H),
X denotes hydrogen or (meth)acryloyl

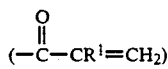

and
n represents 1.

The invention also extends to preparations (II) which contain compounds (Ia) for use as an adhesive component for the treatment of collagen-containing materials, and to processes for the production and the use of the preparations (II).

The claimed preparations (II) contain alkanediyl-bis-carboxamides (Ia) of the formula

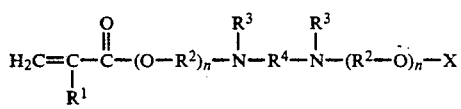

in which
R$^1$ denotes hydrogen or methyl,
R$^2$ and R$^4$ denote divalent aliphatic radicals having one to three carbon atoms,
R$^3$ denotes hydrogen or formyl (—CO—H),
X denotes hydrogen or (meth)acryloyl

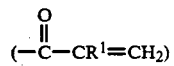

and
n represents 0 or 1, **with the proviso that when R$^3$ equals H, n is zero, and, if appropriate, additives such as initiators, solvents and fillers.

Collagen-containing materials are albuminoid bodies and principal constituents of the human and animal intercellular supporting substances, such as cartilage and bone tissue, skin and dentine. In the context of the present invention, the adhesive components are preferably used for the treatment of dentine in connection with dental repairs.

Particularly in the dental field, setting polymeric materials are used as filling materials in dental repairs. In general, fillings based on acrylates are preferred as setting polymeric materials. However, these polymeric fillings have the disadvantage that they adhere poorly to the dentine. In order to solve this problem, undercuttings to the dental bone have sometimes been carried out hitherto; for this purpose it was necessary to remove considerable amounts of fresh dentine beyond the affected region.

According to another method, the dentine and the enamel surface are etched with acids, such as, for example, phosphoric acid, and the filling is then performed. Apart from the fact that the acid exerts an irritant action in the oral region, it also penetrates easily into the tooth through the dental tubules and damages the nerve (pulp).

In J. Dent. Res. 57, 500–505 (1978), aldehyde group-containing methacrylates of the isomeric hydroxybenzaldehydes are described which can be used as foundations for fillings in the dental field. However, even after such a foundation, the bond between dentine and filling material remains unsatisfactory.

In Scand. J. Dent. Res. 92, 980–983 (1948) and J. Dent. Res. 63, 1087–1089 (1984), foundations based on aqueous formaldehyde or glutaraldehyde and β-hydroxyethyl methacrylate (HEMA) are described.

In addition, compositions formed from an aldehyde and an olefinically unsaturated monomer containing active hydrogen, which bond well to dentine, are described in EP-A-0,141,324.

The new preparations (II) based on alkanediyl-bis-carboxamides effect a strong adhesive bonding of materials which are intended to be attached to collagen, for example an adhesive bonding of dental filling material in a cavity in the tooth.

N,N'-Methylene- and N,N'-ethylene-bis-(meth)-acrylamides are known compounds (Röhm GmbH) and have been employed for the immobilization of thioglycosides (Lee et al., Anal. Biochem. 95 (1979), 260) and as constituents in textile finishing agents (US 518,779, JP 82/95,307, EP 120,316).

Formamide group-containing (meth)acrylic acid esters are known from DE-A-2,507,189. In DE-A-2,507,189 the use of these acrylic acid esters as coatings or adhesives for paper and textiles is also described.

The use of the alkanediyl-bis-carboxamides (Ia) according to the invention as an adhesive component for collagen-containing materials was surprising since they contain no reactive groups which under mild conditions can build up suitable chemical bonds to collagen-containing materials.

For example, the following alkanediyl-bis-carboxamides according to the invention may be mentioned:

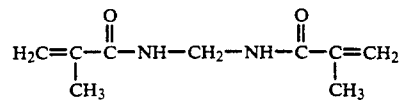

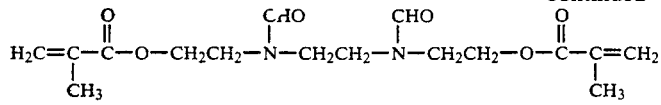

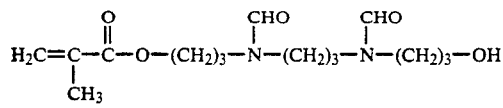

The alkanediyl-bis-carboxamides of the formulae:

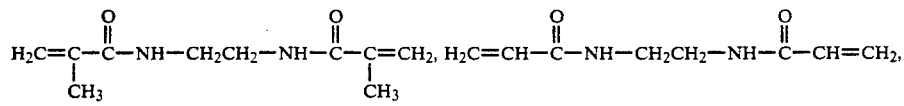

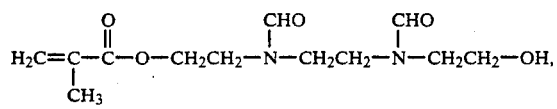

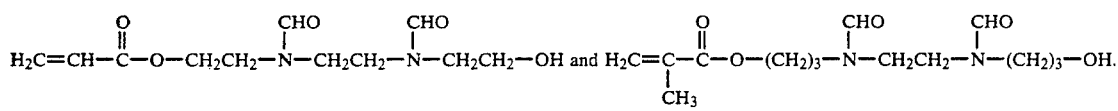

are particularly preferred.

The use of mixtures of these compounds according to the invention, which also contain bifunctional compounds according to the invention as crosslinkers in addition to monofunctional (meth)acrylates or (meth)acrylamides, is particularly preferred.

The new alkanediyl-bis-carboxamides (I) according to the invention can be prepared from dichloroalkanes (III) and alkanolamines (IV). The N,N'-di(hydroxyalkyl)-alkylenediamines (V) first formed (DE 2,548,508) can be reacted to give the products (I) according to the invention by reaction with formic acid esters (VI) and esterification with one or two equivalents of (meth)acrylic acid, or its ester, anhydride or acid chloride (VII).

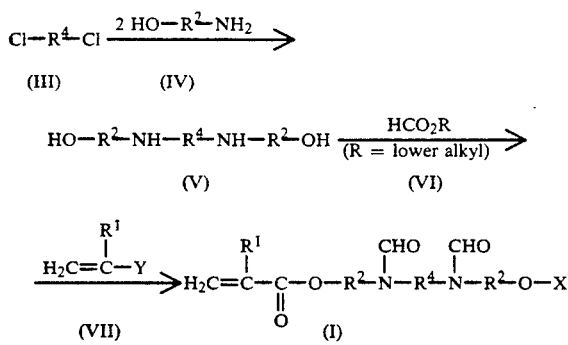

($R^1$, $R^2$, $R^4$ and X have the meanings described above, Y=OH, Oalkyl, Cl or O—$CR^1$=$CH_2$)

Initiators in the context of the present invention are free radical formers which induce a free radical polymerization. Photoinitiators, which induce a free radical polymerization under the action of light, for example UV light, visible light or laser light, are preferred.

The so-called photopolymerization initiators are known per se (Houben-Weyl, Methoden der organischen Chemie (Methods of Organic Chemistry), Volume E 20, page 80 et seq., Georg Thieme Verlag Stuttgart 1987). Preferably, these are mono- or dicarbonyl compounds, such as benzoin and its derivatives, in particular benzoin methyl ether, benzil and benzil derivatives, for example 4,4-oxydibenzil and other dicarbonyl compounds such as diacetyl, 2,3-pentanedione and α-diketo derivatives of norbornane and substituted norbornanes, metal carbonyls such as manganese pentacarbonyl or quinones such as 9,10-phenanthrenequinone and naphthoquinone. Camphorquinone is particularly preferred.

The preparations according to the invention in general contain 0.01 to 2 parts by weight, preferably 0.1 to 0.5 part by weight of the initiator, relative to 100 part by weight of the carboxamide employed. If one of the parts to be joined which is in contact with the adhesive component according to the invention already contains an initiator of the type described, the initiator in the adhesive component can even be completely dispensed with.

The solvents in the context of the present invention should dissolve the component and, because of the application, should be non-toxic. Water and volatile organic solvents such as methanol, ethanol, propanol, isopropanol, acetone, methyl ethyl ketone, methyl acetate or ethyl acetate and tetrahydrofuran, may be mentioned as preferred.

In general, 10 to 1000 parts by weight, preferably 50 to 300 parts by weight, of the solvent are employed, relative to the alkanediyl-bis-carboxamide.

It may be advantageous to add coactivators, which accelerate the polymerization reaction, to the preparations according to the invention. Known accelerators are, for example, amines such as p-toluidine, dimethyl-p-toluidine, trialkylamines such as trihexylamine, polyamines such as N,N,N',N'-tetra-alkylalkylenediamine, barbituric acid and dialkylbarbituric acid.

The coactivators are in general employed in an amount from 0.02 to 4 % by weight, preferably 0.2 to 1 % by weight, relative to the amount of polymerizable compounds.

The compositions according to the invention may contain carbonyl compounds as a further component.

Carbonyl compounds in the context of the present invention are aldehydes and ketones which contain 1 to 20, preferably 1 to 10, and particularly preferably 2 to 6 carbon atoms. The carbonyl function can be bonded to an aliphatic, aromatic and heterocyclic molecule moiety.

Aldehydes which may be mentioned are aliphatic mono- or dialdehydes. Formaldehyde, acetaldehyde, propionaldehyde, 2-methylpropionaldehyde, butyraldehyde, benzaldehyde, vanillin, furfural, anisaldehyde, salicylaldehyde, glyoxal, glutaraldehyde and phthalaldehyde are preferred. Glutaraldehyde is particularly preferred.

Ketones which may be particularly mentioned are aliphatic mono- and diketones. Butanone, acetone, cyclooctanone, cycloheptanone, cyclohexanone, cyclopentanone, acetophenone, benzophenone, 1-phenyl-2-propanone, 1,3-diphenyl-2-propanone, acetylacetone, 1,2-cyclohexanedione, 1,2-cyclopentanedione and camphorquinone are preferred. Cyclopentanone is particularly preferred.

In general, 1 to 1000 parts by weight, preferably 5 to 50 parts by weight, of the carbonyl compounds are employed, relative to the carboxamide group-containing (meth)acrylic acid esters.

As a further component, the compositions according to the invention can contain (meth)acrylic acid esters which can form crosslinkages. (Meth)acrylic acid esters which can form crosslinkages in general contain 2 or more polymerizable active groups in the molecule. Esters of (meth)acrylic acid with dihydric to pentahydric alcohols containing 2 to 30 carbon atoms may be mentioned as preferred. Alkoxy(meth)acrylates and urethane group-containing (meth)acrylates are particularly preferred.

(Meth)acrylic acid esters of the formula

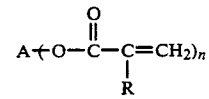

in which

A denotes a straight-chain, branched, cyclic, aliphatic, aromatic or mixed aliphatic-aromatic radical having 2 to 25 C atoms, which can be interrupted by —O—, NH— or O—CO—NH— bridges and can be substituted by hydroxyl, oxy, carboxyl, amino or halogen, R denotes H or methyl and n represents an integer from 2 to 8, preferably 2 to 4, may be mentioned as examples.

Compounds of the following formulae:

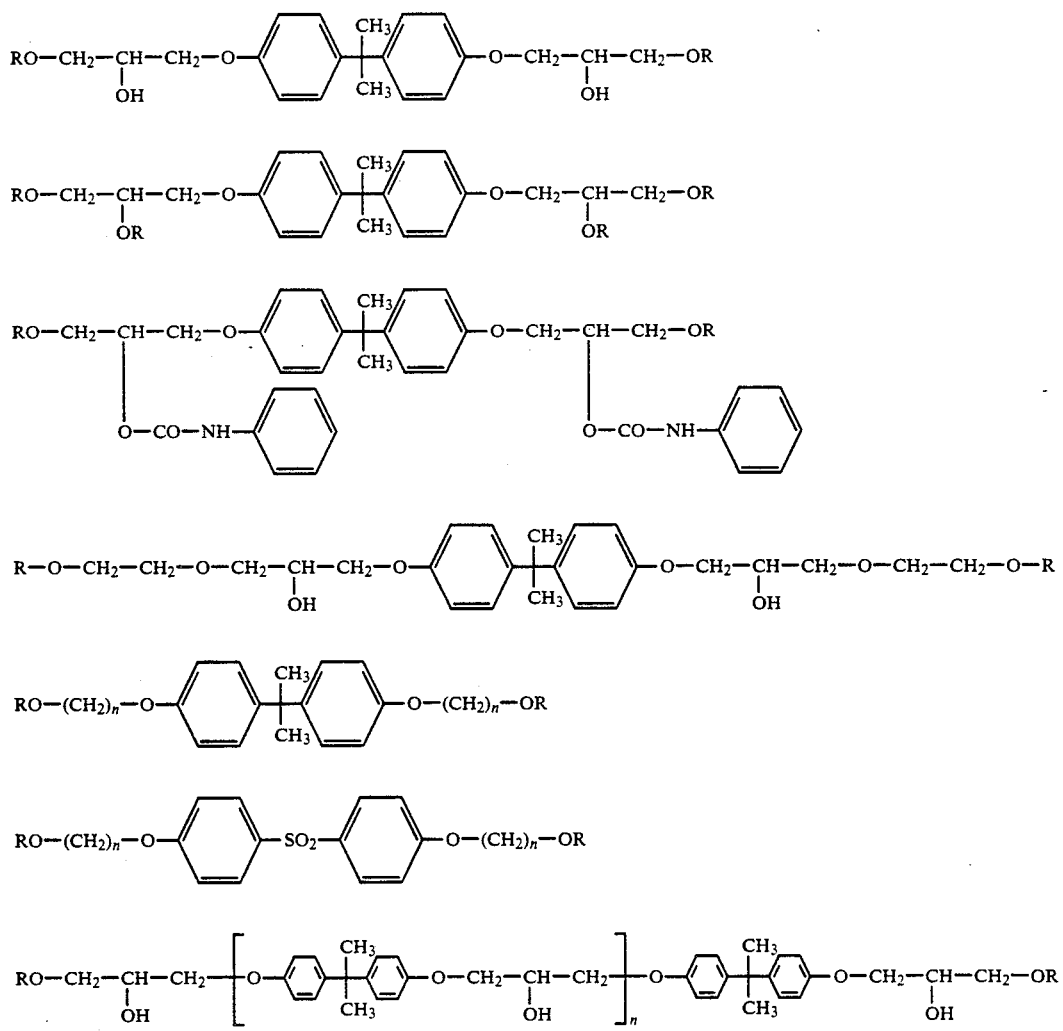

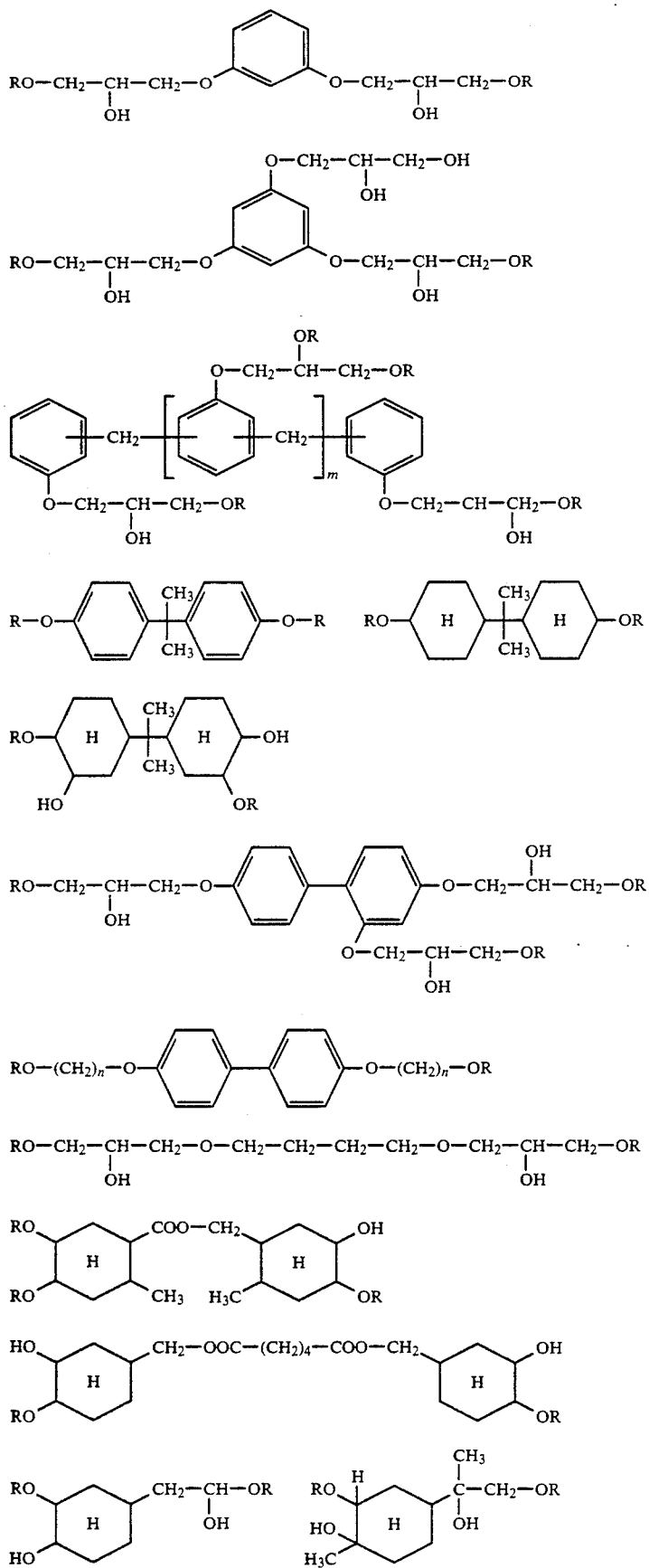

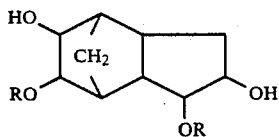
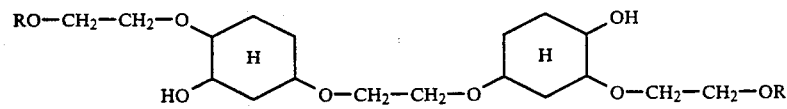
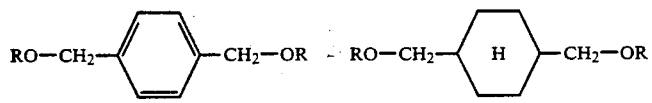
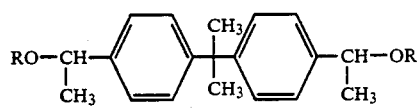
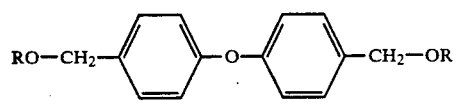
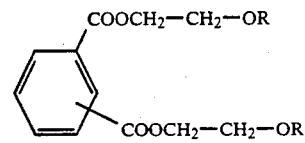
in the ortho-, meta- or para-form
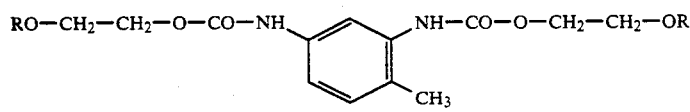
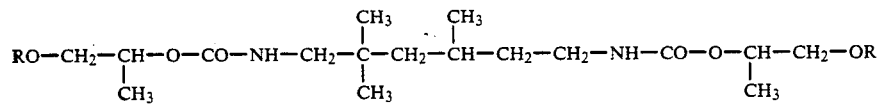
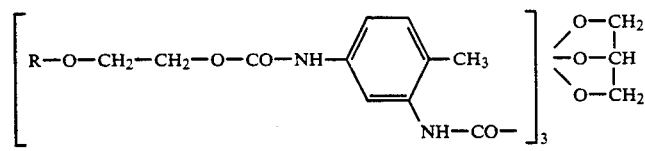
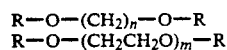
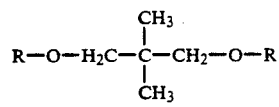
in which
R represents
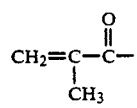
or
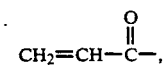
n denotes a number from 1 to 4 and
m denotes a number from 0 to 5,
may be mentioned as preferred.
In addition, derivatives of tricyclodecane (EP-A-0,023,686) and reaction products of polyols, diisocyanates and hydroxyalkyl methacrylates (DE-A-3,703,120, DE-A-3,703,080 and DE-A-3,703,130) may be mentioned. The following monomers may be mentioned as examples:
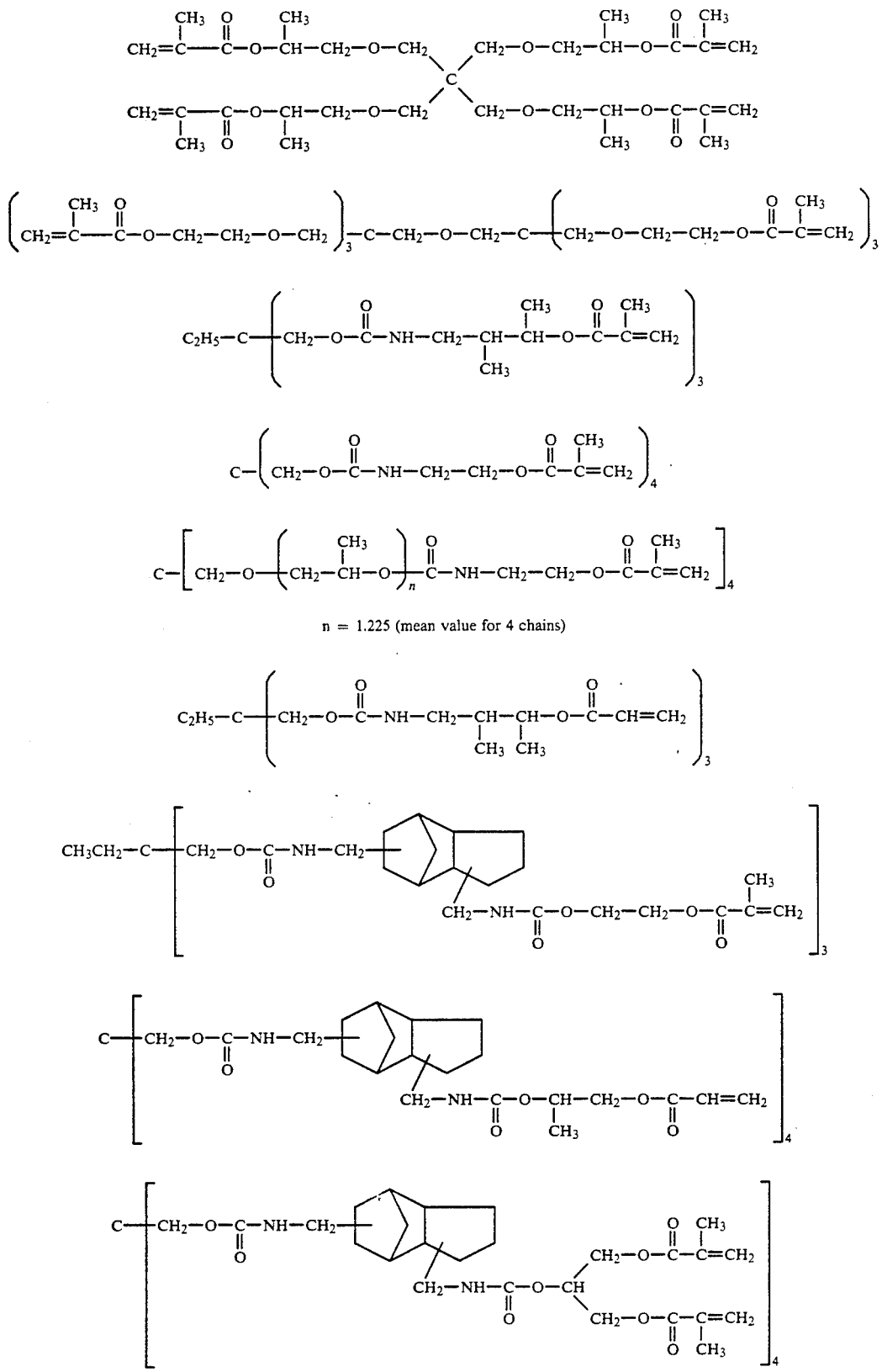
n = 1.225 (mean value for 4 chains)

-continued
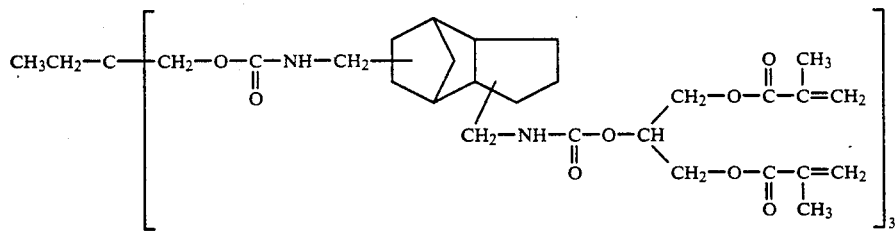
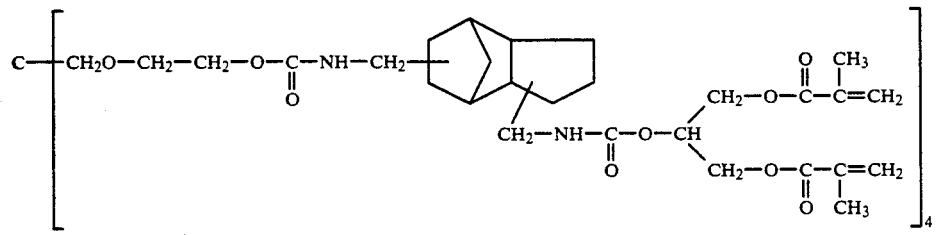
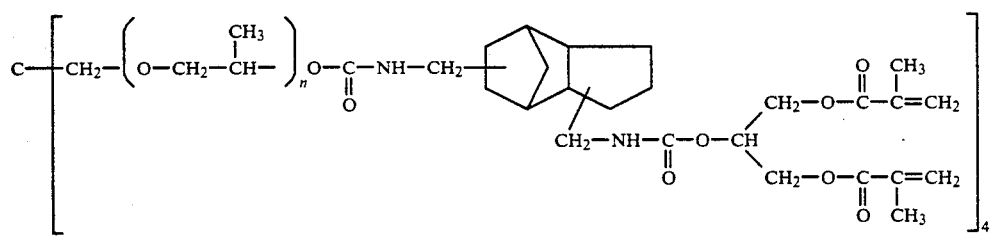
n = 1.225 (statistical mean value for 4 chains)
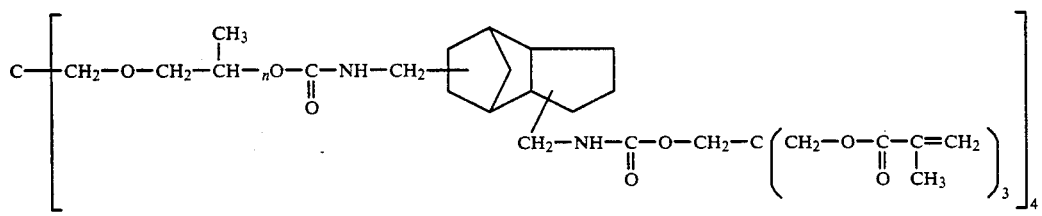
n = 1,225 (mean value)
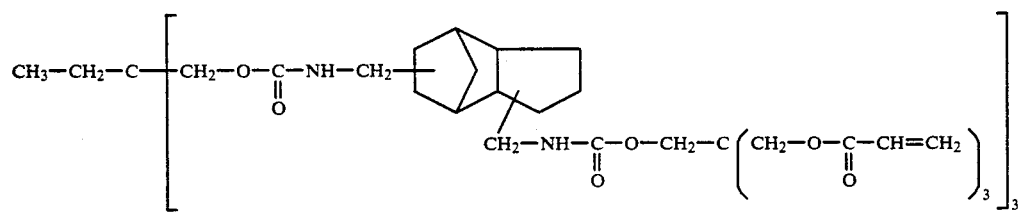
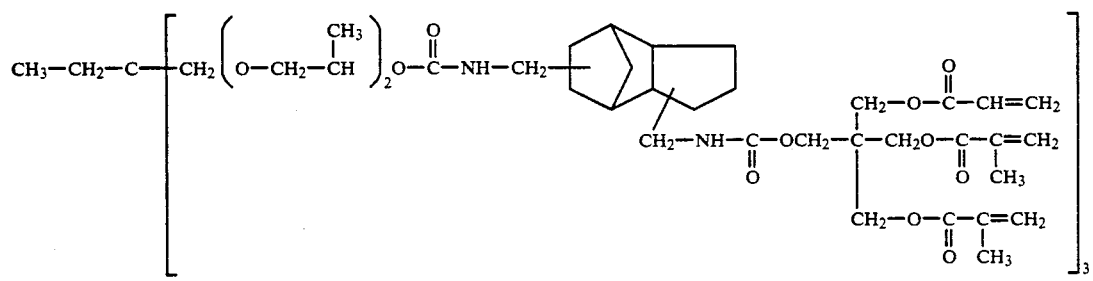

-continued
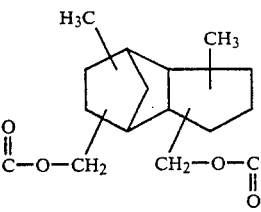
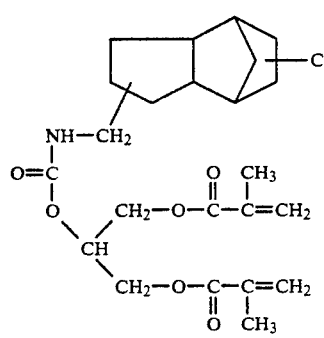
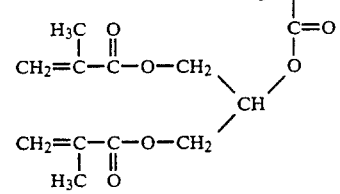
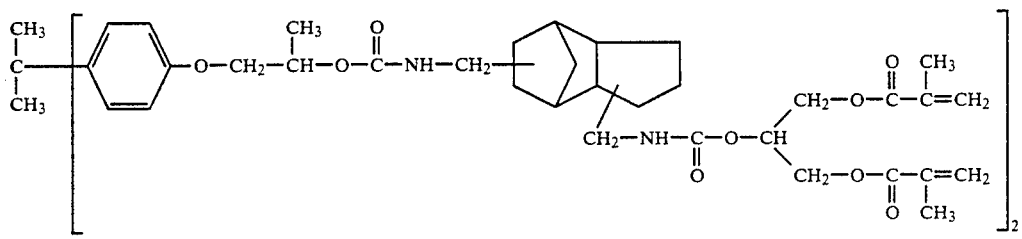
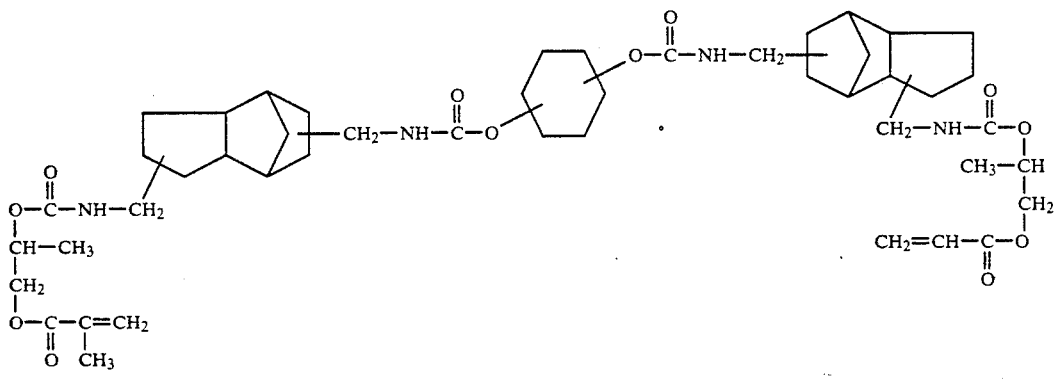
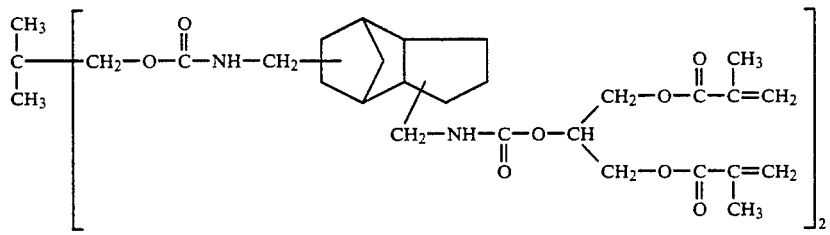
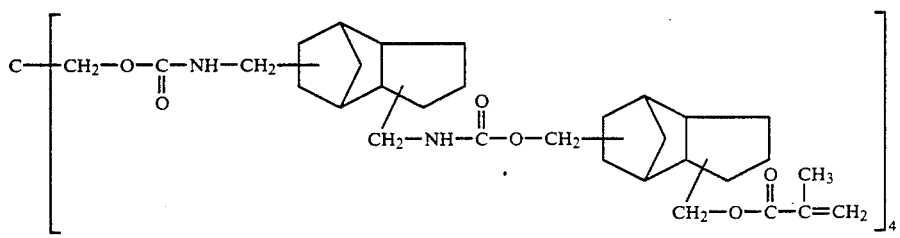

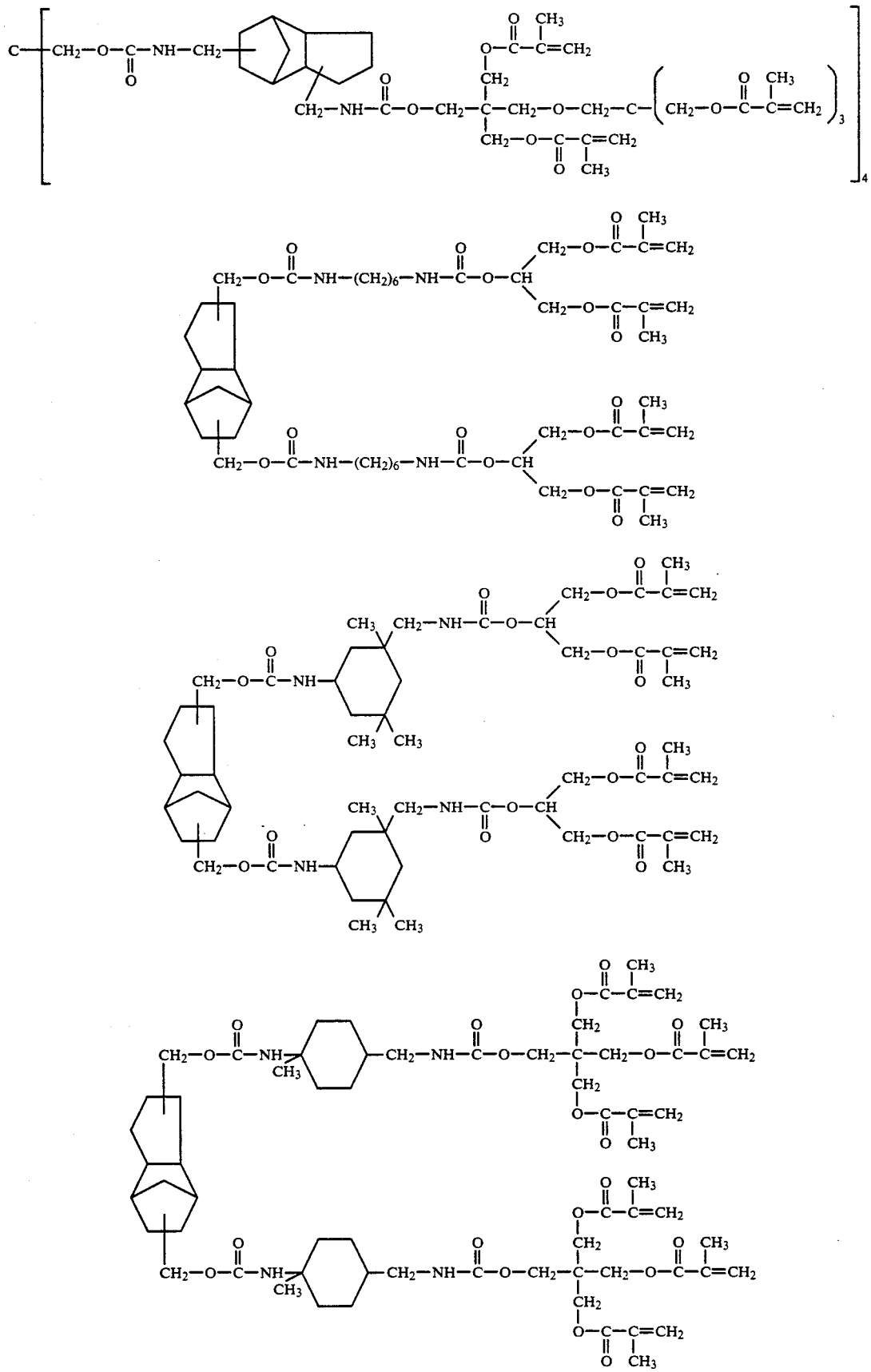

-continued

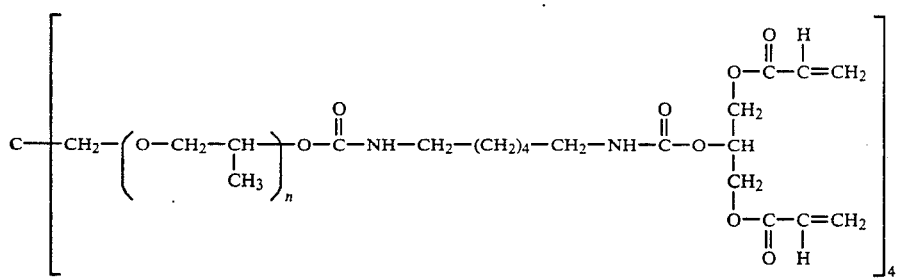

n = 1.225 (statistical mean value for 4 chains)

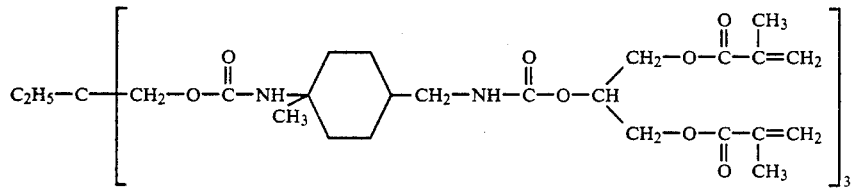

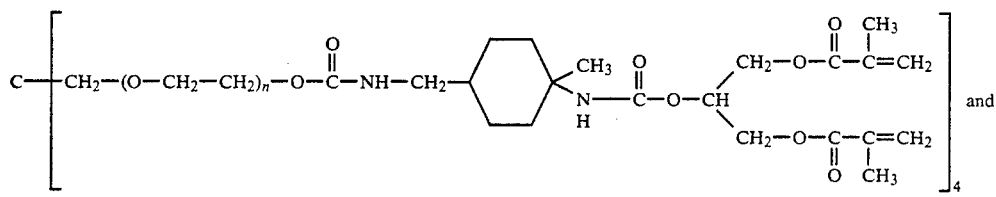

and n = 1.225 (statistical mean value for 4 chains)

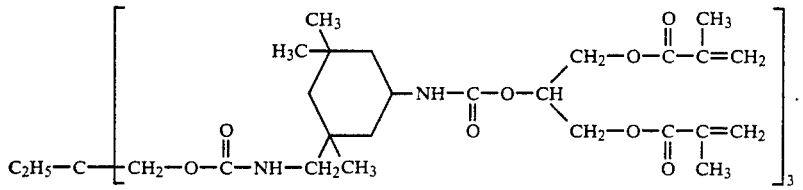

The so-called bis-GMA of the formula

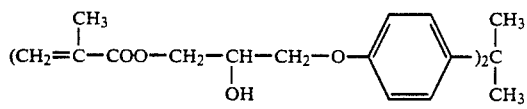

is particularly preferred as a monomer.

Of course, it is possible to employ mixtures of the various (meth)acrylic acid esters which can form cross-linkages. Mixtures of 20 to 70 parts by weight of bis-GMA and 30 to 80 parts by weight of triethylene glycol dimethacrylate may be mentioned as examples.

The preparations according to the invention in general contain 5 to 80 parts by weight, preferably 10 to 60 parts by weight, of carboxyl compounds, relative to the alkanediyl-bis-carboxamides.

The compositions according to the invention may contain fillers as a further component. Fine powders which have a particle diameter in the range from 0.1 to 100 μm (if appropriate also in a polydisperse distribution) are preferred as fillers. Fillers may be fillers customary in the dental field (R. S. Baratz, J. Biomat. Applications, Vol 1, 1987p 316 et seq.) such as inorganic glasses, silica, alumina or quartz powder.

As a result of a proportion of fillers in the preparations according to the invention, adhesive cements result which are particularly suitable for attaching bridges, crowns and other facing materials.

The proportion of the filler is in general 20 to 80 parts by weight, preferably 40 to 70 parts by weight, relative to the total preparation.

The adhesive components according to this invention may furthermore contain up to 10 parts by weight of customary additives such as stabilizers, inhibitors, light screens, colorants, pigments or fluorescent substances.

The preparations according to the invention can be produced by mixing the alkanediyl-bis-carboxamide and the initiator and, if appropriate, the other components by vigorous stirring.

The preparations may also be solvent-free.

The preparations according to the invention can be used as adhesive component for the treatment of collagen-containing materials.

In a particular embodiment, the collagen-containing material is conditioned before the treatment with the preparation according to the invention using a liquid having a pH value in the range from 0.1 to 3.5.

This liquid in general contains acids having a $pK_a$ value of less than 5 and, if appropriate, an amphoteric amino compound having a $pK_a$ value in the range from 9.0 to 10.6 and a $pK_b$ value in the range from 11.5 to 12.5. The conditioning liquid may contain, for example, the following acids:

phosphoric acid, nitric acid, pyruvic acid, citric acid, oxalic acid, ethylenediaminetetraacetic acid, acetic acid, tartaric acid, malic acid and maleic acid.

Amphoteric amino compounds which may be mentioned are preferably compounds of the formula $$\begin{array}{c} H \\ | \\ R^{12}-C-R^{11} \\ | \\ R^{13}-NH \end{array}$$

in which $R^{11}$ represents a carboxyl group, $R^{12}$ denotes hydrogen, or a lower alkyl radical optionally substituted by hydroxyl, thio, methylthio, carboxyl, amino, phenyl, hydroxy-phenyl or the groups

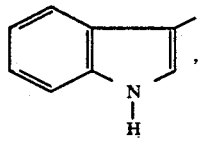 , 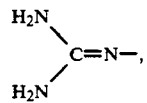

$R^{13}$ denotes hydrogen or phenyl,
where the radicals $R^{11}$ and $R^{13}$ can be linked via a propyl radical, or
in which
$R^{11}$ represents hydrogen,
$R^{12}$ represents the group

—A—NH$_3$Y, in which
A represents a doubly-bonded alkylene radical having 1 to 6 carbon atoms and
Y represents halogen, and
$R^{13}$ denotes hydrogen.

The following amphoteric amino compounds may be mentioned as examples: glycine, serine, threonine, cysteine, tyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid may furthermore contain substances from the group comprising the polyethylene glycols and metal hydroxides. In particular, the above-mentioned polybasic acids can also be employed partly as metal salts as long as free acid functions remain.

Conditioning liquids which contain at least one of the acids from the group comprising pyruvic acid, ethylenediaminetetraacetic acid and citric acid and, if appropriate, an amphoteric amino compound from the group comprising glycine, N-phenylglycine and proline, are particularly preferred.

The application of the preparations according to the invention can be carried out, for example, as follows In a dental repair, for example, after a mechanical cleaning of the collagen-containing dental material, the conditioning fluid is first applied using some absorbent cotton and allowed to act for a short time (for example 60 seconds), and the dental material is rinsed with water and dried in a stream of air. The preparation according to the invention is then applied in a thin layer, for example using a small brush, and dried in a stream of air. After the treatment according to the invention, the actual filling material, for example plastic filling materials customary in the dental field (K. Eichner, "Zahnärztliche Werkstoffe und ihre Verarbeitung" (Dental materials and their processing), Vol. 2, p. 135 et seq., Hüthig Verlag, 5th Edition 1985) is applied.

In a similar fashion, the preparations according to the invention can be used for attaching crowns, bridges and similar aids.

EXAMPLE 1

Synthesis of Ethanediyl-N-[β-(N-formyl)-amino-ethyl 2-methyl-2-propenoate]-N'-[β-hydroxyethyl-(N'-formyl)-amine]

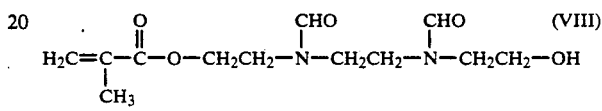

Preliminary step: 90.10 g (1.500 mol) of methyl formate were added dropwise to 116.16 g (0.750 mol) of bis-(2-hydroxyethyl)-ethylenediamine in 200 ml of methanol and the mixture was heated to reflux for seven hours. After stripping off all easily volatile constituents at 0.1 Torr and 30° C., 147.05 g (96% of theory) of N,N-ethanediyl-bis(β-hydroxyethyl-N-formylamine) (IX) remain in the form of a pale oil.

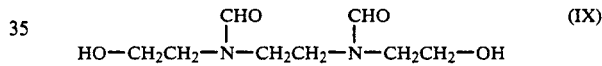

IR (film): γ=3310, 2902, 1657, 1414, 1398, 1193, 1145, 1060, 858 cm$^{-1}$.

$^1$H-NMR (CDCl$_3$, 200 MHz): δ=3.42, 3.56, 3.71(3 m, together 14 H, CH$_2$ and OH), 8.02, 8.08 (2 s, together 2 H, CHO in various rotamers) ppm.

MS (70 e V - after silylation): m/e=348 (M$^{30}$), 333 (M—CH$_3$), 188, 146, 144, 126, 116 (CH$_2$CH$_2$OTMS+) 73 (TMS+).

Subsequent step:

55.15 g (0.270 mol) of the precursor (IX) in 150 ml of dry dichloromethane were initially introduced at −35° C. together with 37.00 g (0.366 mol) of triethylamine and 27 mg of 2,6-di-tert.-butyl-4-methylphenol, and 28.23 g (0.270 mol) of methyacryloyl chloride were added dropwise in such a way that the temperature did not rise above −30° C. The mixture was stirred for a further 2 hours at −35° C., then the precipitate which deposited at 0° C. was filtered off with suction and the organic solution was extracted with water several times. The aqueous phase was perforated with dichloromethane for 18 hours, and the organic phase was dried and concentrated to give 30.1 g (41% of theory) of the desired product (VIII) which was a slightly yellowish oil.

IR (film): γ=3400, 2960, 1728, 1670, 1440, 1408, 1320, 1300, 1163, 1078, 950, 818 cm$^{-1}$.

$^1$H-NMR (CDCl$_3$, 200 MHz): δ=1.93 (bs 3 H CH$_3$) 3.3–3.8 (m, 10 H, NCH$_2$ and CH$_2$OH), 4.39 (m, 2 H, COCH$_2$), 5.61, 6.08 (2 m each 1 H, vinyl. H), 8.00–8.10 (m, 2 H, CHO in various rotamers) ppm.

EXAMPLE 2

Synthesis of
N,N'-Ethanediyl-bis[β-(N-formyl)amino-ethyl 2-methyl-2-propenoate]

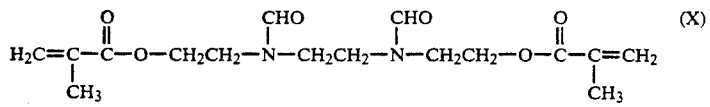

51.50 g (0.252 mol) of the precursor (IX) in 200 ml of dry trichloromethane together with 61.00 g (0.603 mol) of triethylamine and 30 mg of 2,6-di-tert.-butyl-4-methylphenol were initially introduced at -35° C and 52.27 g (0.500 mol) of methacryloyl chloride were added dropwise between −30° C. and −35° C. over the course of an hour. The mixture was stirred at −35° C. for a further 2 hours, the precipitate which deposited was separated off and the organic phase was concentrated after aqueous extraction to give 58.97 g (69% of theory) of the desired product (X). The initially yellowish oil slowly crystallized out.

Melting point: 59°-60° C.

IR (K Br): $\gamma = 2960$, 1728, 1672, 1432, 1401, 1320, 1298, 1160, 1085, 1031, 948, 813 cm$^{-1}$.

$^1$H-NMR (CDCl$_3$, 200 MHz): $\delta = 1.93$ (bs, 6 H, CH$_3$), 3.4–3.7 (m, 8 H, CH$_2$N), 4.27 (m, 4 H, CH$_2$O), 5.62, 6.09 (2 m, each 2 H, vinyl.H), 8.04, 8.09 (2 s, together 2 H, CHO in various rotamers) ppm.

EXAMPLES 3 to 5

Production of the preparations (II)

The adhesives according to the invention are produced by intensive mixing of the constituents shown in the following examples.

EXAMPLE 3

14 g of water
65 g of acetone
6 g of 25% strength by weight aqueous glutaraldehyde solution
15 g of N,N'-1,2-ethanediyl-bis-2-methyl-2-propenamide (XI)
40 mg of camphorquinone

EXAMPLE 4

18 g of water
65 g of acetone
17 g of N,N'-1,2-ethanediyl-bis-2-methyl-2-propenamide (XI)
40 mg of camphorquinone

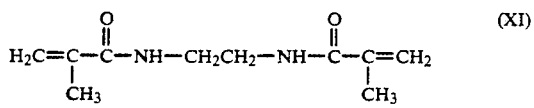

EXAMPLE 5

45 g of water
51 g of product (VIII)
4 g of product (X)
170 mg of camphorquinone

EXAMPLE 6

The suitability of the adhesives (II) corresponding to Examples 1 to 5 is tested by determining the bonding strength of the light-activated plastic filling material based on multi-functional methacrylic acid esters and barium aluminosilicate LUMIFOR Light Curing Composite Universal (U) ® on dentine.

Extracted human teeth which have been kept in 1% chloramine solution for a maximum of 3 months after extraction are used for the tests. After these teeth have been carefully cleaned under running water, they were stored in physiological saline solution up to the point of embedding in epoxy resin (Lekutherm X 257).

Using abrasive paper of different grain size, the tooth is ground wet until a sufficiently large dentine surface is exposed for bonding a synthetic filling material cylinder of 3.5 mm. The exposed dentine surface was finally prepared wet using silicon carbide paper 600.

The dentine is successively pretreated with the EDTA conditioning fluid GLUM ® cleanser (60 seconds cleaning with a cotton-wool pellet, rinsing with water, air drying) and the adhesive (60 seconds period of action, air drying).

In order to prepare the sample for the tensile bonding test, the dentine sample prepared as described previously is tensioned in a stand using a cylindrical, divisible Teflon mould. This Teflon mould, altogether 5 mm high, is conically shaped in the upper half so that a tensile test can be carried out using a correspondingly shaped adapter.

A sealing material based on polyfunctional methacrylic acid ester BAYER Resin L ® is applied in a thin layer to the pretreated dentine surface using a brush and additionally distributed using a stream of air.

The sealing material is first irradiated at a distance of 5 mm from the dentine surface using a polymerization light (Translux Cl, Kulzer). Incremental mould filling and light activation of the synthetic filling material is then carried out.

The light activation period for the synthetic filling material is set to a total of 160 seconds on the basis of the large volume.

After termination of the light activation, the sample is removed and stored in a water bath at 23° C. until the tensile test.

The tensile bonding strength, the force used to break the sample divided by the contact area with the dentine, was measured using a feed rate of 1 mm/min.

The breaking surface on the dentine is then checked using a light microscope to evaluate the cause of failure. In this connection, multiple cohesive fractures were to be observed, i.e. the bondings produced using the adhesive components according to the invention were stronger than the bonded parts to be joined themselves. This shows the high efficiency of the adhesive components according to the invention.

It will be appreciated that the instant specification is set forth by way of illustration and not limitation, and that various modifications and changes may be made without departing from the spirit and scope of the present invention.

What is claimed is:

1. An alkanediyl bis-carboxamide of the formula

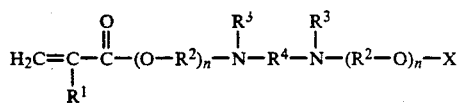

in which
R$^1$ denotes hydrogen or methyl,
R$^2$ and R$^4$ denote divalent aliphatic radicals having two or three carbon atoms,
R$^3$ denotes formyl (—CO—H),
X denotes hydrogen or (meth)acryloyl

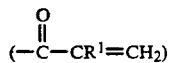

and
n represents 1.

2. An adhesive composition for the treatment of collagen-containing materials comprising an alkanediyl-bis-carboxamide of the formula

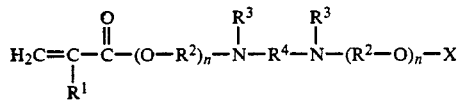

in which
R$^1$ denotes hydrogen or methyl,
R$^2$ and R$^4$ denote divalent aliphatic radicals having one to three carbon atoms,
R$^3$ denotes hydrogen or formyl (—CO—H),
X denotes hydrogen or (meth)acryloyl

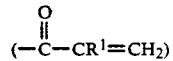

and n represents 0 or 1,
with the proviso that when R$^3$ equals H, n is zero, and an additive comprising an initiator, solvent or filler.

3. A composition according to claim 2, in which
R$^1$ denotes hydrogen or methyl,
R$^3$ denotes hydrogen,
R$^4$ denotes ethylene (—CH$_2$CH$_2$—),
X denotes hydrogen or (meth)acryloyl

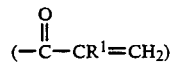

and
n represents 0.

4. A composition according to claim 2, in which
R$^1$ denotes hydrogen or methyl,
R$^2$ and R$^4$ denote ethylene (—CH$_2$CH$_2$—),
R$^3$ denotes formyl (—CO—H),
X denotes hydrogen or (meth)acryloyl

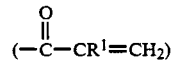

and
n represents 1.

5. A composition according to claim 2, further including a free radical former comprising a mono- or dicarbonyl compound as an initiator.

6. A composition according to claim 2, dissolved in a solvent.

7. A composition according to claim 2, additionally containing a coactivator.

8. A composition according to claim 2, containing a carbonyl compound.

9. A composition according o claim 2, additionally containing at least one (meth)acrylic acid ester which can form crosslinkages.

10. A composition according to claim 2, further containing a filler.

* * * * *

UNITED STATES PATENT AND TRADEMARK OFFICE
CERTIFICATE OF CORRECTION

PATENT NO. : 5,071,933

DATED : December 10, 1991

INVENTOR(S) : Müller et al.

It is certified that error appears in the above-identified patent and that said Letters Patent is hereby corrected as shown below:

Col. 26, line 37   Delete " o " and substitute -- to --

Signed and Sealed this

Thirteenth Day of July, 1993

*Attest:*

*Attesting Officer*

MICHAEL K. KIRK

*Acting Commissioner of Patents and Trademarks*